United States Patent
Ferguson et al.

(10) Patent No.: US 6,900,181 B2
(45) Date of Patent: *May 31, 2005

(54) PHARMACEUTICAL COMPOSITION

(75) Inventors: Mark W. J. Ferguson, Derbyshire (GB); Sarah G. Jones, Derbyshire (GB); Sally Freeman, Cheshire (GB)

(73) Assignee: Renovo Limited, Manchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/389,903

(22) Filed: Mar. 18, 2003

(65) Prior Publication Data

US 2004/0072763 A1 Apr. 15, 2004

Related U.S. Application Data

(63) Continuation of application No. 09/653,991, filed on Sep. 1, 2000, now Pat. No. 6,566,339, which is a continuation of application No. 09/011,138, filed as application No. PCT/GB96/01840 on Jul. 31, 1996, now Pat. No. 6,140,307.

(30) Foreign Application Priority Data

Aug. 4, 1995 (GB) .............................. 9516012

(51) Int. Cl.$^7$ .......................... A61K 31/70; C07H 15/00
(52) U.S. Cl. .......................... 514/23; 514/25; 536/1.11; 536/17.1
(58) Field of Search ..................... 514/23, 25; 536/1.11, 536/17.1

(56) References Cited

U.S. PATENT DOCUMENTS 4,703,040 A    10/1987  Markov

FOREIGN PATENT DOCUMENTS

| WO | WO-A-9001938 | 8/1990 |
| WO | WO-A-9109604 | 7/1991 |
| WO | WO A-9318777 | 9/1993 |
| WO | WO-A-9514036 | 5/1995 |

*Primary Examiner*—Elli Peselev
(74) *Attorney, Agent, or Firm*—Nixon & Vanderhye P.C.

(57) ABSTRACT

The present invention concerns analogues of M6P for use in promoting the healing of wounds or fibrotic disorders with reduced scarring, together with methods for doing same.

21 Claims, 3 Drawing Sheets

(a)

(b)

(c)

(d)

TRANS
(e)

CIS
(f)

PHARMACEUTICAL COMPOSITION

This application is a continuation of application Ser. No. 09/653,991, filed Sep. 1, 2000, now U.S. Pat. No. 6,566,339, which is a continuation of Ser. 09/011,138, filed May 29, 1998, now U.S. Pat. No. 6,140,307, which is a 371 of PCT/GB96/01840, filed Jul. 31, 1996, which claims priority from GB 9516012.3, filed Aug. 4, 1995.

The present invention concerns pharmaceutical compositions for promoting the healing of wounds or fibrotic disorders, in particular for promoting the healing of wounds or fibrotic disorders with reduced scarring.

By "wounds or fibrotic disorders" is meant any condition which may result in the formation of scar tissue. In particular, this includes the healing of skin wounds, the repair of tendon damage, the healing of crush injuries, the healing of eye wounds including wounds to the cornea, the healing of central nervous system (CNS) injuries, conditions which result in the formation of scar tissue in the CNS, scar tissue formation resulting from strokes, and tissue adhesion, for example, as a result of injury or surgery (this may apply to e.g. tendon healing and abdominal strictures and adhesions). Examples of fibrotic disorders include pulmonary fibrosis, glomerulonephritis, cirrhosis of the liver, and proliferative vitreoretinopathy.

By "reduced scarring" is meant reduced level of scarring relative to an untreated wound or fibrotic disorder.

In particular, there is a lack of compositions for promoting the healing of wounds or fibrotic disorders with reduced scarring. Scar tissue formation, although providing mechanical strength to a healed wound, can be unsightly and may impair the function of the tissue.

This is particularly the case in wounds which result in scar tissue formation in the CNS, the scar tissue inhibiting the reconnection of severed or re-growing nerve ends, so significantly affecting their function.

Compositions for promoting the healing of wounds or fibrotic disorders may also be used together with compositions for use in the treatment of chronic wounds, for example venous ulcers, diabetic ulcers and bed sores (decubitus ulcers), especially in the elderly and wheel chair bound patients. Such compositions may be extremely useful in patients where wound healing is either slow or in whom the wound healing process has not yet started. Such compositions may be used to "kick-start" wound healing and may then be used in combination with the compositions of the present invention. Hence not only may a chronic wound be healed, but it may be healed with reduced scarring.

The activation of LTGF-$\beta$ (Latent Transforming Growth Factor-$\beta$) to active TGF-$\beta$ is a critical step in the healing process. LTGF-$\beta$ (which comprises TGF-$\beta$ bound to the LAP (Latency Associated Peptide) which in turn may be bound to the LTBP (LTGF-$\beta$ Binding Protein)) binds to cell-surface M6P (mannose-6-phosphate) receptors via M6P-containing carbohydrates in the LAP (Purchio, M. F. et al.,1988, J. Biol. Chem., 263: 14211–14215; Dennis, P. A. and Rifkin, D. B., 1991, Proc. Natl. Acad. Sci. USA, 88: 580–584; Shah, M. et al., 1992, Lancet, 339: 213–214; Shah, M. et al., 1994, J. Cell Sci., 107: 1137–1157). This binding allows the activation of the LTGF-$\beta$ a process also involving transglutaminase and plasminogen/plasmin.

Due to the binding of LTGF-$\beta$ to the M6P receptor, M6P itself may play a significant role in the healing process by competing with the M6P-containing carbohydrates in the LAP for the M6P receptor binding site. By increasing the quantity of M6P at a site (by "site" in this context is meant a site of wounding or a fibrotic disorder), the binding of LTGF-$\beta$ to the M6P receptor may be inhibited (or at least reduced), and the levels of fibrotic and non-fibrotic TGF-$\beta$ affected.

Although M6P is extremely useful, it is quickly metabolised and so previous attempts to increase the levels of M6P at a wound site have focused upon providing a constant supply of M6P to the wound site by the use of slow/sustained/biocompatible non-inflammatory delivery systems. Such slow/sustained delivery systems are both costly and inconvenient and are extremely difficult to produce since it is difficult to achieve slow release from a non-inflammatory/biocompatible vehicle.

The present inventor has found that, surprisingly, analogues of M6P may be used to promote the healing of wounds or fibrotic disorders with reduced scarring, the analogues having similar yet distinct structures and functioning as M6P and/or inhibiting the degradation of M6P.

According to the present invention there is provided an analogue of M6P for use in promoting the healing of wounds or fibrotic disorders with reduced scarring.

The analogue may be a phosphonate analogue of M6P or a salt thereof. Such an analogue may, for example, be any one of the molecules of FIGS. 1(a)–(f) or salt thereof. Surprisingly, it has been found that phosphonate analogues of M6P are capable of binding to the M6P isomerase binding site. This allows them to competitively inhibit the binding of M6P to the binding site and competitively inhibit M6P breakdown (i.e. M6P metabolism), therefore increasing the half-life of M6P. Even more surprisingly, these phosphonate analogues of M6P, despite their molecular similarity to M6P and despite their ability to bind to the M6P isomerase binding site, have significantly greater half-lives than M6P (i.e. are broken down at a significantly slower rate than M6P).

The analogue may have a significantly greater half-life than M6P The analogue may have a half-life at least approximately 10 times that of M6P. It may, for example, have a half-life at least approximately 100 or 1000 times greater than M6P. It may be metabolised by M6P isomerase at a significantly slower rate than M6P. The analogue may bind the M6P isomerase receptor binding site. It may bind to the cell-surface M6P receptor binding site.

The analogue may bind to the M6P isomerase receptor binding site. It may bind to the cell-surface M6P receptor binding site.

The analogue having a greater binding affinity than M6P for a M6P receptor. The analogue may have a greater affinity than M6P for the M6P isomerase receptor binding site. The analogue may have a binding affinity for the M6P receptor approximately 2 or 3 times that of M6P.

The analogue may be the phosphonate analogue of M6P of FIG. 1(b) or a salt thereof, having a half-life approximately 1000 times that of M6P.

The analogue may be the phosphonate analogue of M6P of FIG. 1(b) or a salt thereof, having a half-life approximately 1000 times that of M6P and a binding affinity for the M6P isomerase receptor binding site approximately 3 times that of M6P.

The analogue may increase the half-life of M6P in an environment containing M6P isomerase. The analogue may be for use in increasing the half-life of M6P in an environment containing M6P isomerase.

The analogue may be for use in the environment of the human or animal body.

The analogue may be for use to promote the healing of wounds or fibrotic disorders with reduced scarring.

The analogue may be an inhibitor of M6P breakdown. It may be an inhibitor of M6P metabolism. It may be an inhibitor of M6P isomerase.

The analogue may be used in conjunction with a composition for promoting the healing of wounds or fibrotic disorders with reduced scarring. Such a composition may comprise M6P. For example, an analogue according to the present invention may comprise a phosphonate analogue of M6P in conjunction with M6P itself.

The analogue may be for use in conjunction with a composition for promoting the healing of chronic wounds.

The analogue may be for use in conjunction with a pharmaceutically acceptable carrier, diluent or excipient.

This means that a single dose of a phosphonate analogue may have a long-lasting effect upon a wound site, providing significant clinical and therapeutic advantages. This in turn means that instead of the present continual supply of M6P to a wound site, a site may be given a single dose, or several doses, of a phosphonate analogue of M6P.

By reducing the dosage of M6P to a wound site, the osmotic effect upon the surrounding tissue at the site may be significantly reduced when compared to the osmotic effect of a continual supply of M6P.

The analogue may be used in conjunction with a pharmaceutically acceptable carrier, diluent or excipient.

Hence the analogue may be functionally equivalent to M6P, yet may have a significantly greater half-life and/or receptor binding affinity than M6P. The analogue may not only function as M6P, but may also act to increase the half-life and efficacy of any added or endogenous M6P by inhibiting the metabolism of M6P by, for example, M6P isomerase.

Also provided according to the present invention is a method for promoting the healing of wounds or fibrotic disorders with reduced scarring comprising the use of an analogue of M6P according to any one of the preceding claims.

The method may comprise administering an analogue of M6P to a site of wounding or fibrosis.

The method may comprise the use of an analogue of M6P either immediately before or immediately after wounding/onset. It may comprise the use of an analogue of M6P within approximately 120 hours of wounding/onset, although it may be preferable to apply it within a shorter time, for example 120, 96, 72, 48, 24 or 12 hours post-wounding/onset. By "onset" is meant the onset of a fibrotic disorder.

The efficacy of the treatment in promoting healing with reduced scarring may be significantly enhanced by increasing M6P levels at a site immediately following wounding when TGF-$\beta_1$ complexed to LAP is released from degranulating platelets. The TGF-$\beta_1$ complexed to LAP is either free in the tissue fluid, bound to the fibrin clot/platelet complex, or is endocytosed into surrounding cells. e.g. fibroblasts. monocytes and macrophages, by the M6P receptor. This degranulation and release of fibrotic TGF-$\beta_1$ upon initial wounding has a number of effects which affect subsequent healing. In particular, the TGF-$\beta_1$ attracts monocytes and macrophages to the site, which in turn release more TGF-$\beta_1$. By inhibiting this initial activation of TGF-$\beta$, which is predominantly TGF-$\beta_1$, the ratio of fibrotic: non-fibrotic growth factors at a site may be altered in favour of non-fibrotic growth factors and enhanced healing with reduced scarring effected.

The method may be used in conjunction with a method for promoting the healing of wounds or fibrotic disorders with reduced scarring.

The method may be used in conjunction with a method for promoting the healing of chronic wounds.

Experimental work undertaken in treating wounds with non-phosphorylated mannose and glucose resulted in retarded healing when compared with controls. Galactose-6-phosphate and glycerol-3-phosphate have no effect upon either wound healing or scarring.

The invention will be further apparent from the following example, which shows by way of example only, one form of analogue of M6P which is metabolised at a significantly slower rate and has a greater M6P receptor binding affinity than M6P and may be used to inhibit M6P metabolism.

EXPERIMENTAL

Figure 3:
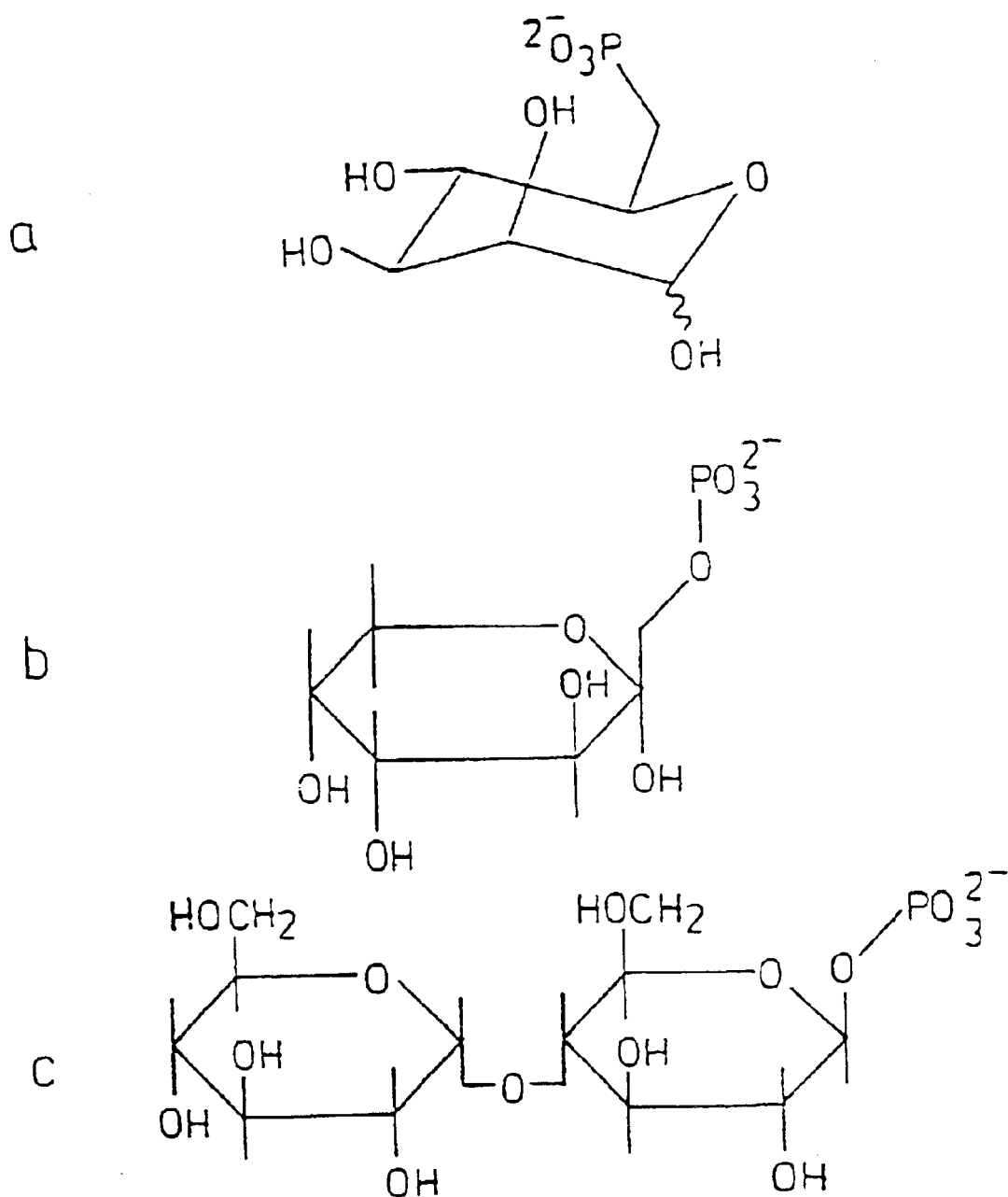
FIG. 3 shows (a) non-isosteric mannose phosphonate; (b) fructose-1-phosphate; and (c) maltose-1-phosphate.

The wound healing and anti-scarring properties of isosteric mannose phosphonate (FIG. 1(b)) and non-isosteric mannose phosphonate (FIG. 3a), fructose-1-phosphate (FIG. 3b) and maltose-1-phosphate (FIG. 3c) were tested as described below.

Figure 1:
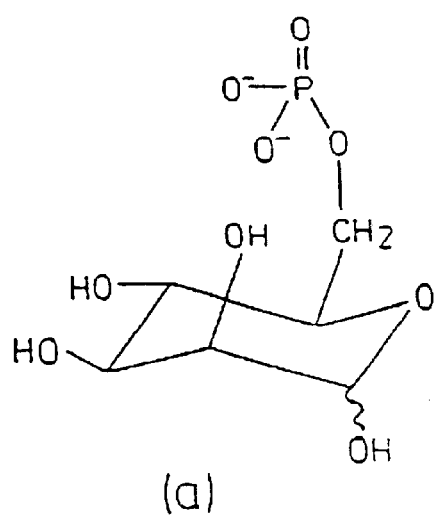
FIG. 1 shows various phosphonate analogues of M6P. Figures are labelled (a)–(f) running from left to right, top to bottom.
Figure 1:
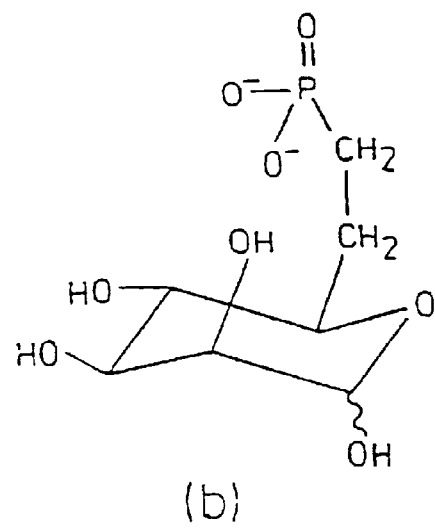
Figure 1:
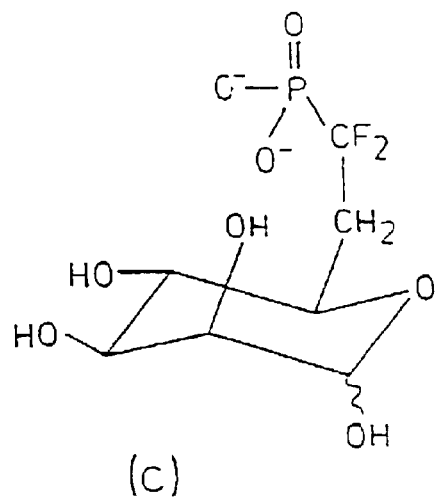
Figure 1:
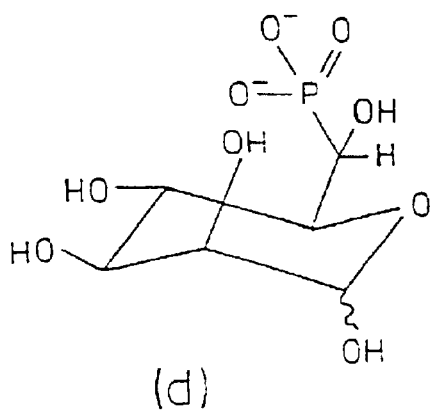
Figure 1:
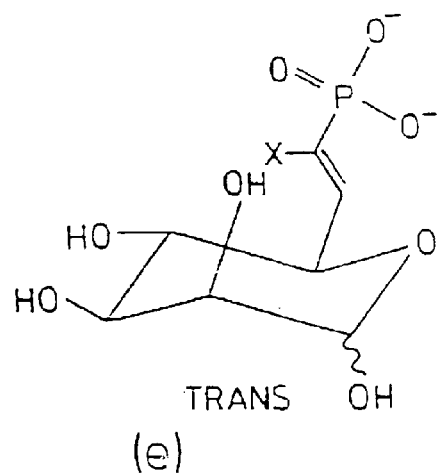
Figure 1:
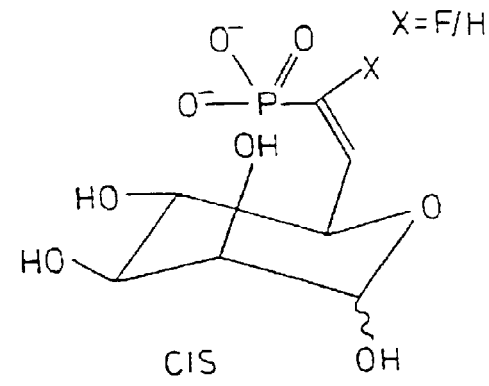
Figure 2:
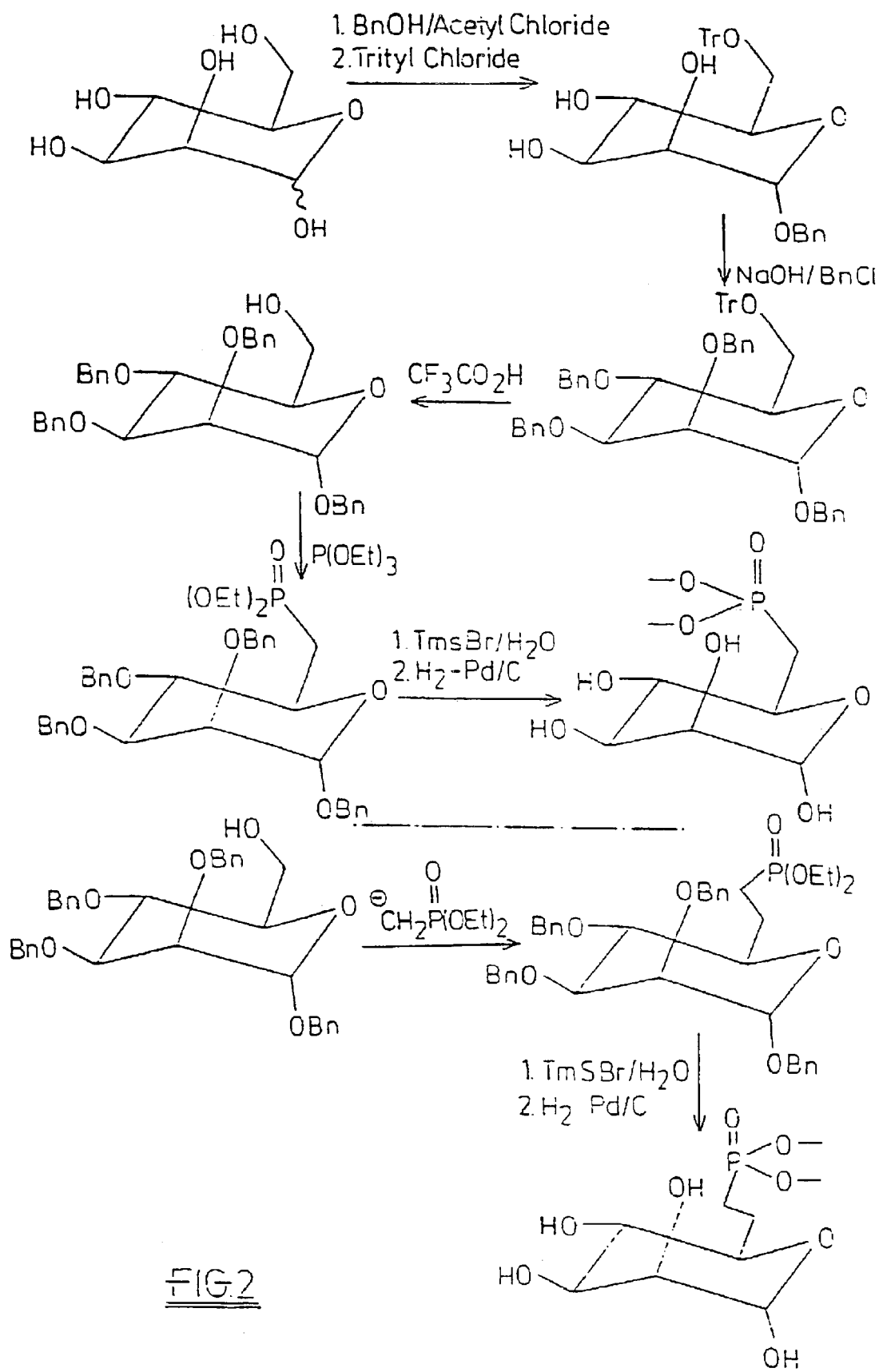
FIG. 2 shows methods of synthesis of same.

Additionally, the M6P phosphonate analogue of FIG. 1(b) was prepared and a receptor binding assay performed with M6P isomerase to analyse its binding affinity for the M6P receptor and also to analyse its half-life. Standard methods were used to obtain the data.

Method

Adult male Sprague Dawley rats (200–250 g) were anaesthetised using equal parts halothane, nitrous oxide and oxygen. Four linear full thickness incisions, 1 cm in length to the depth of the panniculus carnosus were made on the dorsal skin, 1 cm from the midline and 5 and 8 cm from the base of the skull. The wounds were left unsutured to heal by secondary intention. Experimental treatments were administered by intradermal injection to the wound margins (50 $\mu$l down each wound margin). At selected time points animals were killed by chloroform overdose. Wounds were excised from the surrounding tissue and bisected. Half the wounds were rapidly frozen in OCT for cryosection and immunocytochemistry and half fixed in formaldehyde for wax embedding and histology. Wax sections were routinely stained with haematoxylin and eosin, picrosirius red and Massons Lille trichrome, to display collagen fibre thickness, density and orientation to enable assessment of scar quality.

Fructose-1-phosphate (F1P) and maltose-1-phosphate (Malt1P) were purchased from Sigma Chemical Company. A range of doses (10 mM, 20 mM and 40 mM) was studied for each sugar, with PBS (phosphate buffered saline) as a control. Treatments were administered at the time of wounding and each day for the following seven days. Two animals per dose were studied at each of the three time points (7, 40 and 80 days post wounding) for each compound. Total n=12.

Isosteric mannose phosphonate was synthesised and supplied by Dr Sally Freeman, Department of Pharmacy, University of Manchester. A range of doses (20 mM, 10 mM, and 10 mM+10 mM M6P) were studied, with PBS as a negative control, and 10 mM M6P and 20 mM M6P as positive controls. Treatments were administered at the time of wounding and each day for the following two days. One animal per dose was studied at each of the two time points (7 and 80 days post wounding). Total n=4.

Non-isosteric mannose phosphonate was synthesised and supplied by Dr Sally Freeman. Department of Pharmacy, University of Manchester. A single concentration (20 mM)

of this compound was studied, with PBS as a control. The time of administration varied to the previous experiments. Animals were split into three groups and treated on day 0 alone, days 0, 2 and 4, or days 0 to 7 inclusive. Two animals per treatment regime were studied at each of the three time points (3, 7 and 80 days) Total n=18.

In addition to the animal studies an ELISA-type assay using purified M6P/IGF II (insulin-like growth factor II) receptor was developed to determine if these analogues of M6P bind to the M6P/IGF II receptor.

Results

Fructose-1-Phosphate and Maltose-1-Phosphate

At 7 days post wounding histological analysis showed that neither F1P or Malt1P had any effect on wound healing, when compared with PBS controls. Immunocytochemical analysis also showed that treated wounds resembled controls. Staining for fibronectin was consistent between treatments and controls as were monocyte/macrophage profiles. At 40 days post wounding histological analysis was inconsistent, with no clear trend. At 80 days post wounding Malt1P appeared to improve the dermal architecture very slightly whilst F1P appeared to reduce scarring more significantly, particularly at the highest dose studied (40 mM).

Isosteric Mannose Phosphonate

At 7 days post wounding histological analysis revealed that none of the treated wounds appeared different to PBS controls. At 80 days post wounding the isosteric analogue appeared to improve the dermal architecture when compared with controls, and showed a similar improvement in scarring as the M6P treatments.

Non-Isosteric Mannose Phosphonate

Initial histological analysis of wounds treated with 20 mM non-isosteric analogue from days 0 to 7 post wounding indicate an anti-scarring effect, especially with the 20 mM treatment on days 0 to 7 post wounding.

The results so far obtained indicate that despite the similarity of the mannose-6-phosphate analogues tested (F1P, Malt1P, and the isosteric and non-isosteric mannose phosphonate analogues), the greater efficacy of the mannose phosphonate analogues may be due to their fulfilling an additional role or having special properties with regard to their interactions with other molecules.

Receptor Binding Assay

Initial results from the receptor binding assay showed that F1P binds the M6P/IGF II receptor with similar affinity as M6P, whereas Malt1P does not bind to this receptor. The results also showed that the analogue of FIG. 1(b) had a binding affinity approximately 3 times that of M6P for the M6P receptor binding site. Surprisingly, the results also showed that despite this significantly increased binding affinity and despite its structural similarity to M6P, the analogue had a half-life of approximately 1000 times that of M6P.

This suggests that other analogues of M6P, in particular other phosphonate analogues of M6P, may have similar properties and may therefore have great potential as inhibitors of scarring.

What is claimed is:

1. A method for promoting the healing of wounds or fibrotic disorders with reduced scarring comprising administering to a subject in need of treatment a therapeutically effective amount of a Mannose-6-Phosphonate.

2. The method according to claim 1 wherein the phosphonate is administered either immediately before or immediately after wounding or onset of the fibrotic disorder.

3. The method according to claim 1 wherein the phosphonate is administered within 120 hours of wounding or onset of the fibrotic disorder.

4. The method according to claim 1 wherein the phosphonate has a significantly greater half-life than mannose-6-phosphate.

5. The method according to claim 4 wherein the phosphonate has a half-life at least approximately 10 times that of mannose-6-phosphate.

6. The method according to claim 5 wherein the phosphonate has a half-life at least approximately 100 or 1000 times that of mannose-6-phosphate.

7. The method according to claim 1 wherein the phosphonate is metabolized by mannose-6-phosphate isomerase at a significantly slower rate than mannose-6-phosphate.

8. The method according to claim 1 wherein the phosphonate binds to the mannose-6-phosphate isomerase receptor binding site.

9. The method according to claim 1 wherein the phosphonate binds to the cell-surface mannose-6-phosphate receptor binding site.

10. The method according to claim 1 wherein the phosphonate has a greater binding affinity than mannose-6-phosphate for a mannose-6-phosphate receptor.

11. The method according to claim 1 wherein the phosphonate has a greater affinity than mannose-6-phosphate for the mannose-6-phosphate isomerase receptor binding site.

12. The method according to claim 1 wherein the phosphonate has a binding affinity for the mannose-6-phosphate receptor approximately 2 or 3 times that of mannose-6-phosphate.

13. The method according to claim 1 wherein the phosphonate increases the half-life of mannose-6-phosphate in an environment containing mannose-6-phosphate isomerase.

14. The method according to claim 1 wherein the phosphonate is for use in increasing the half-life of mannose-6-phosphate in an environment containing mannose-6-phosphate isomerase.

15. The method according to claim 1 wherein the phosphonate is an inhibitor of mannose-6-phosphate breakdown.

16. The method according to claim 1 wherein the phosphonate is an inhibitor of mannose-6-phosphate metabolism.

17. The method according to claim 1 wherein the phosphonate is an inhibitor of mannose-6-phosphate isomerase.

18. The method according to claim 16 wherein the phosphonate is administered in conjunction with a composition for promoting the healing of wounds or fibrotic disorders with reduced scarring.

19. The method according to claim 1 wherein the phosphonate is administered in conjunction with a composition for promoting the healing of chronic wounds.

20. A mannose-6-phosphonate or a salt thereof.

21. A medicament comprising a mannose-6-phosphonate in conjunction with a pharmaceutically acceptable carrier, diluent or excipient.

* * * * *